United States Patent
Wisniewski et al.

(10) Patent No.: US 8,748,564 B2
(45) Date of Patent: Jun. 10, 2014

(54) OXYTOCIN RECEPTOR AGONISTS

(75) Inventors: Kazimierz Wisniewski, San Diego, CA (US); Claudio Daniel Schteingart, San Diego, CA (US); Sudarkodi Alagarsamy, San Diego, CA (US); Robert Galyean, Escondido, CA (US)

(73) Assignee: Ferring B.V., Hoofddorp (NL)

( * ) Notice: Subject to any disclaimer, the term of this patent is extended or adjusted under 35 U.S.C. 154(b) by 56 days.

(21) Appl. No.: 13/496,269

(22) PCT Filed: Sep. 21, 2010

(86) PCT No.: PCT/US2010/049714
§ 371 (c)(1), (2), (4) Date: May 3, 2012

(87) PCT Pub. No.: WO2011/035330
PCT Pub. Date: Mar. 24, 2011

(65) Prior Publication Data
US 2012/0214733 A1 Aug. 23, 2012

Related U.S. Application Data

(60) Provisional application No. 61/244,327, filed on Sep. 21, 2009.

(51) Int. Cl.
| | | |
|---|---|---|
| A61K 38/11 | (2006.01) | |
| A61P 25/00 | (2006.01) | |
| A61P 1/00 | (2006.01) | |
| A61P 15/10 | (2006.01) | |
| A61P 15/04 | (2006.01) | |
| A61P 15/00 | (2006.01) | |
| A61P 15/14 | (2006.01) | |
| A61P 7/04 | (2006.01) | |
| A61P 25/22 | (2006.01) | |
| A61P 35/00 | (2006.01) | |
| C07K 7/16 | (2006.01) | |
| A61P 29/00 | (2006.01) | |

(52) U.S. Cl.
CPC .................................. *A61K 38/11* (2013.01)
USPC ...................................................... 530/200

(58) Field of Classification Search
None
See application file for complete search history.

(56) References Cited

U.S. PATENT DOCUMENTS

| 4,349,544 A | 9/1982 | Cort et al. | |
|---|---|---|---|
| 4,402,942 A | 9/1983 | Melin | |
| 4,483,794 A | 11/1984 | Barth et al. | |
| 2002/0128444 A1* | 9/2002 | Gingras et al. | 530/350 |

FOREIGN PATENT DOCUMENTS

FR 2485527 B1 8/1985

OTHER PUBLICATIONS

Gimpl ("Oxytocin receptor ligands: a survey of the patent literature" (2008) Expert Opin Ther Patents 18(11): 1239-1251).*
Organic-chemistry.org, "Protecting Groups" (Apr. 29, 2007), http://web.archive.org/web/20130117100507/http://www.organic-chemistry.org/protectivegroups/ downloaded Jul. 10, 2013.*
Gimpl G: "Oxytocin receptor ligands: A survey of the patent literature", Expert Opinion on Therapeutic Patents 200811 GB LNKD-DOI:10.1517/13543776.18.11.1239, vol. 18, No. 11, Nov. 2008, pp. 1239-1251, XP002627531, ISSN: 1354-3776 the whole document pp. 1244; table 1 (2008).
Barth T et al., "Milk-ejecting and uterotonic activities of oxytocin analogues in rats", Endocrinologia Experimentalis, Veda, Bratislava, SK, vol. 9, No. 1, Jan. 1, 1975, pp. 35-42, XP009145655, ISSN: 0013-7200 the whole document pp. 40; tables 1-2 (1975).
Barth et al., 'Biological Activities and Protracted Action of Carba-Analogues of Deamino-Oxytocin with O-Methyltyrosine in Position 2', Collection Czechaslay. Chem. Commun., vol. 45, pp. 3045-3050 (1980).
International Search Report issued in corresponding International Application No. PCT/US2010/049714 on Apr. 5, 2011.
International Preliminary Report on Patentability issued in corresponding International Application No. PCT/US2010/049714 on Mar. 27, 2012.
Office Action issued Jan. 9, 2014 in corresponding New Zealand Application No. 598579.

* cited by examiner

*Primary Examiner* — Jean Witz
*Assistant Examiner* — Mindy Newman
(74) *Attorney, Agent, or Firm* — Fish & Richardson P.C.

(57) ABSTRACT

The present invention relates to oxytocin receptor agonist compounds, pharmaceutical compositions comprising the same, use of such compounds for the manufacture of a medicament for treatment of inter alia, abdominal pain, irritable bowel syndrome (IBS), autism, erectile dysfunction, female sexual dysfunction, labor induction and maintenance, lactation induction and maintenance, postpartum hemorrhage, Post Traumatic Stress Disorder (PTSD), pain, anxiety and other conditions, as well as to methods for the treatment of such conditions, wherein such compounds are administered. The compounds are represented by the general formula (I), as further defined in the specification:

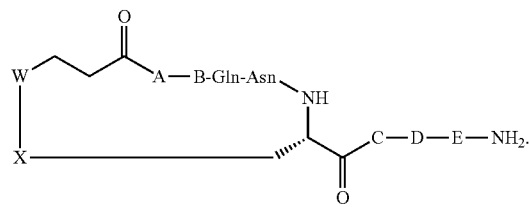

17 Claims, No Drawings

SEQUENCE LISTING

```
<160> NUMBER OF SEQ ID NOS: 26

<210> SEQ ID NO 1
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: /note="Tyr(Me)"
<220> FEATURE:
<221> NAME/KEY: MOD_RES
<222> LOCATION: (7)..(7)
<223> OTHER INFORMATION: /note="Thz"

<400> SEQUENCE: 1

Cys Tyr Ile Gln Asn Cys Pro Leu Gly
1               5

<210> SEQ ID NO 2
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: /note="Tyr(Me)"
<220> FEATURE:
<221> NAME/KEY: MOD_RES
<222> LOCATION: (8)..(8)
<223> OTHER INFORMATION: /note="Gly(cPe)"

<400> SEQUENCE: 2

Cys Tyr Ile Gln Asn Cys Pro Gly Gly
1               5

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: /note="Tyr(Me)"
<220> FEATURE:
```

```
<221> NAME/KEY: MOD_RES
<222> LOCATION: (7)..(7)
<223> OTHER INFORMATION: /note="Pro(4-N3)"

<400> SEQUENCE: 3

Cys Tyr Ile Gln Asn Cys Pro Leu Gly
1               5

<210> SEQ ID NO 4
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: /note="Hol"

<400> SEQUENCE: 4

Cys Tyr Ile Gln Asn Cys Pro Leu Gly
1               5

<210> SEQ ID NO 5
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: /note="Phe(4-Et)"

<400> SEQUENCE: 5

Cys Phe Ile Gln Asn Cys Pro Leu Gly
1               5

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: /note="Phe(4-CH2OH)"
<220> FEATURE:
<221> NAME/KEY: MOD_RES
<222> LOCATION: (7)..(7)
<223> OTHER INFORMATION: /note="Hyp"

<400> SEQUENCE: 6

Cys Phe Ile Gln Asn Cys Pro Leu Gly
1               5

<210> SEQ ID NO 7
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: MOD_RES
<222> LOCATION: (2)..(2)
<223> OTHER INFORMATION: /note="Cpa"
<220> FEATURE:
<221> NAME/KEY: MOD_RES
<222> LOCATION: (7)..(7)
<223> OTHER INFORMATION: /note="Pro(4-F)"

<400> SEQUENCE: 7

Cys Ala Ile Gln Asn Cys Pro Leu Gly
1               5

<210> SEQ ID NO 8
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: /note="Phe(4-Br)"
<220> FEATURE:
<221> NAME/KEY: MOD_RES
<222> LOCATION: (7)..(7)
<223> OTHER INFORMATION: /note="Pro(4-F)"

<400> SEQUENCE: 8

Cys Phe Ile Gln Asn Cys Pro Leu Gly
1               5

<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: /note="Phe(4-Et)"
<220> FEATURE:
<221> NAME/KEY: MOD_RES
<222> LOCATION: (7)..(7)
<223> OTHER INFORMATION: /note="Pro(4-F)"

<400> SEQUENCE: 9

Cys Phe Ile Gln Asn Cys Pro Leu Gly
1               5

<210> SEQ ID NO 10
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: /note="Cpa"
<220> FEATURE:
<221> NAME/KEY: MOD_RES
<222> LOCATION: (3)..(3)
<223> OTHER INFORMATION: /note="Gly(cPe)"
<220> FEATURE:
<221> NAME/KEY: MOD_RES
<222> LOCATION: (7)..(7)
<223> OTHER INFORMATION: /note="Hyp"
```

```
<400> SEQUENCE: 10

Cys Ala Gly Gln Asn Cys Pro Leu Gly
1               5

<210> SEQ ID NO 11
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: /note="Cpa"
<220> FEATURE:
<221> NAME/KEY: MOD_RES
<222> LOCATION: (7)..(7)
<223> OTHER INFORMATION: /note="Hyp"
<220> FEATURE:
<221> NAME/KEY: MOD_RES
<222> LOCATION: (8)..(8)
<223> OTHER INFORMATION: /note="Gly(cPe)"

<400> SEQUENCE: 11

Cys Ala Ile Gln Asn Cys Pro Gly Gly
1               5

<210> SEQ ID NO 12
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: /note="Cpa"
<220> FEATURE:
<221> NAME/KEY: MOD_RES
<222> LOCATION: (7)..(7)
<223> OTHER INFORMATION: /note="Hyp"
<220> FEATURE:
<221> NAME/KEY: MOD_RES
<222> LOCATION: (8)..(8)
<223> OTHER INFORMATION: /note="Gly(cPe)"

<400> SEQUENCE: 12

Cys Ala Ile Gln Asn Cys Pro Gly Gly
1               5

<210> SEQ ID NO 13
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: /note="Cpa"
<220> FEATURE:
<221> NAME/KEY: MOD_RES
<222> LOCATION: (7)..(7)
<223> OTHER INFORMATION: /note="Hyp"

<400> SEQUENCE: 13
```

Cys Ala Ile Gln Asn Cys Pro Ile Gly
1               5

<210> SEQ ID NO 14
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: /note="Cpa"
<220> FEATURE:
<221> NAME/KEY: MOD_RES
<222> LOCATION: (7)..(7)
<223> OTHER INFORMATION: /note="Hyp"

<400> SEQUENCE: 14

Cys Ala Ile Gln Asn Cys Pro Ile Gly
1               5

<210> SEQ ID NO 15
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: /note="Cpa"
<220> FEATURE:
<221> NAME/KEY: MOD_RES
<222> LOCATION: (3)..(3)
<223> OTHER INFORMATION: /note="Gly(cPe)"
<220> FEATURE:
<221> NAME/KEY: MOD_RES
<222> LOCATION: (7)..(7)
<223> OTHER INFORMATION: /note="Hyp"

<400> SEQUENCE: 15

Cys Ala Gly Gln Asn Cys Pro Leu Gly
1               5

<210> SEQ ID NO 16
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: /note="Phe(4-CH2OH)"
<220> FEATURE:
<221> NAME/KEY: MOD_RES
<222> LOCATION: (7)..(7)
<223> OTHER INFORMATION: /note="Hyp"

<400> SEQUENCE: 16

Cys Phe Ile Gln Asn Cys Pro Leu Gly
1               5

<210> SEQ ID NO 17
<211> LENGTH: 9
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (9)..(9)
<223> OTHER INFORMATION: /note="AzGly"

<400> SEQUENCE: 17

Cys Tyr Ile Gln Asn Cys Pro Leu Gly
1               5

<210> SEQ ID NO 18
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: /note="Cpa"
<220> FEATURE:
<221> NAME/KEY: MOD_RES
<222> LOCATION: (9)..(9)
<223> OTHER INFORMATION: /note="AzGly"

<400> SEQUENCE: 18

Cys Ala Ile Gln Asn Cys Pro Leu Gly
1               5

<210> SEQ ID NO 19
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: /note="2-Thi"
<220> FEATURE:
<221> NAME/KEY: MOD_RES
<222> LOCATION: (9)..(9)
<223> OTHER INFORMATION: /note="AzGly"

<400> SEQUENCE: 19

Cys Ala Ile Gln Asn Cys Pro Leu Gly
1               5

<210> SEQ ID NO 20
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (9)..(9)
<223> OTHER INFORMATION: /note="AzGly"

<400> SEQUENCE: 20

Cys Tyr Ile Gln Asn Cys Pro Leu Gly
1               5
```

```
<210> SEQ ID NO 21
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: /note="Cpa"
<220> FEATURE:
<221> NAME/KEY: MOD_RES
<222> LOCATION: (3)..(3)
<223> OTHER INFORMATION: /note="Gly(cBu)"
<220> FEATURE:
<221> NAME/KEY: MOD_RES
<222> LOCATION: (7)..(7)
<223> OTHER INFORMATION: /note="Hyp"

<400> SEQUENCE: 21

Cys Ala Gly Gln Asn Cys Pro Leu Gly
1               5

<210> SEQ ID NO 22
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: /note="Cpa"
<220> FEATURE:
<221> NAME/KEY: MOD_RES
<222> LOCATION: (9)..(9)
<223> OTHER INFORMATION: /note="AzGly"

<400> SEQUENCE: 22

Cys Ala Ile Gln Asn Cys Pro Leu Gly
1               5

<210> SEQ ID NO 23
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: /note="Dmt"

<400> SEQUENCE: 23

Cys Tyr Ile Gln Asn Cys Pro Leu Gly
1               5

<210> SEQ ID NO 24
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
```

```
<222> LOCATION: (2)..(2)
<223> OTHER INFORMATION: /note="Aph"
<220> FEATURE:
<221> NAME/KEY: MOD_RES
<222> LOCATION: (7)..(7)
<223> OTHER INFORMATION: /note="Hyp(Me)"

<400> SEQUENCE: 24

Cys Ala Ile Gln Asn Cys Pro Leu Gly
1               5

<210> SEQ ID NO 25
<211> LENGTH: 9
<212> TYPE: PRT
<213> ORGANISM: Unknown
<220> FEATURE:
<221> NAME/KEY: source
<223> OTHER INFORMATION: /note="Description of Unknown: Mammalian
      oxytocin peptide"

<400> SEQUENCE: 25

Cys Tyr Ile Gln Asn Cys Pro Leu Gly
1               5

<210> SEQ ID NO 26
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: /note="Hyp"
<220> FEATURE:
<221> NAME/KEY: MOD_RES
<222> LOCATION: (9)..(9)
<223> OTHER INFORMATION: /note="AzGly"

<400> SEQUENCE: 26

Cys Tyr Ile Gln Asn Cys Pro Leu Gly
1               5
```

OXYTOCIN RECEPTOR AGONISTS

CROSS REFERENCE TO PRIOR APPLICATIONS

This is a U.S. National Phase application under 35 U.S.C. §371 of International Patent Application No. PCT/US2010/049714, filed Sep. 21, 2010, and claims the priority of U.S. Provisional Application No. 61/244,327, filed Sep. 21, 2009 both of which are incorporated by reference herein in their entirety. The International Application published in English on Mar. 24, 2011 as WO 2011/035330 under PCT Article 21(2).

FIELD OF THE INVENTION

The present invention relates to oxytocin receptor agonist compounds, pharmaceutical compositions comprising the same, use of such compounds for the manufacture of a medicament for treatment of, inter alia, abdominal pain, irritable bowel syndrome (IBS), autism, erectile dysfunction, female sexual dysfunction, labor induction and maintenance, lactation induction and maintenance, postpartum hemorrhage, Post Traumatic Stress Disorder (PTSD), pain, anxiety and other conditions, as well as to methods for the treatment of such conditions, wherein such compounds are administered.

BACKGROUND

Peptidic oxytocin receptor agonists include the natural hormone oxytocin, and carbetocin.

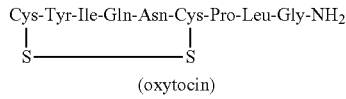

(oxytocin)

Oxytocin is a potent uterotonic agent, clinically used to induce labour, and has been shown to enhance the onset and maintenance of lactation (Gimpl et al., *Physiol. Rev.*, 81, (2001), 629-683; Ruis et al., *BMJ*, 283, (1981), 340-342). Carbetocin (1-deamino-1-carba-2-tyrosine(O-methyl)-oxytocin) is also a potent uterotonic agent clinically used for the control of uterine atony and excessive bleeding. Further research indicates that oxytocin agonists are useful for the treatment of inflammation and pain, including abdominal and back pain (Yang, *Spine*, 19, (1994), 867-71); sexual dysfunction, both male (Lidberg et al., *Pharmakopsychiat.*, 10, (1977), 21-25) and female (Anderson-Hunt, et al., *BMJ*, 309 (1994), 929); irritable bowel syndrome (IBS; Louvel et al., *Gut*, 39, (1996), 741-47), constipation and gastrointestinal obstruction (Ohlsson et al., *Neurogastroenterol. Motil.*, 17, (2005), 697-704); autism (Hollander et al., *Neuropsychopharm.*, 28, (2008), 193-98), stress (including Post Traumatic Stress Disorder, PTSD; Pitman et al., *Psychiatry Research*, 48, 107-117), anxiety (including anxiety disorder) and depression (Kirsch et al., *J. Neurosci.*, 25(49), 11489-93; Waldherr et al., *PNAS*, 104, (2007), 16681-84); surgical blood loss, the control of post-partum haemorrhage (Fujimoto et al., *Acta Obstet. Gynecol.*, 85, (2006), 1310-14), labor induction and maintenance (Flamm et al., *Obstet. Gynecol.*, 70, (1987) 709-12), wound healing and infection; mastitis and placenta delivery; and osteoporosis. Additionally, oxytocin agonists may be useful for the diagnosis of both cancer and placental insufficiency.

Efforts continue to identify and develop compounds with sufficient potency at the human oxytocin receptor. Analogues of oxytocin have been synthesised. Such analogues are described in Grzonka et al., *J. Med. Chem.*, 26, (1983), 555-559 and *J. Med. Chem.*, 26, (1983), 1786-1787, and in Engstrøm et al., E. J. Pharmacol., 355, (1998), 203-210. Additionally, oxytocin analogues with antagonist activity at the oxytocin receptor have been described in Fragiadaki et al., *E. J. Med. Chem.*, (2007), 799-806.

The present invention may provide potent and long duration of action compounds, providing feasible alternatives and/or improvements in the treatment of, e.g., abdominal pain, irritable bowel syndrome (IBS), autism, erectile dysfunction, female sexual dysfunction, labor induction and maintenance, lactation induction and maintenance, postpartum hemorrhage, Post Traumatic Stress Disorder (PTSD), pain, anxiety, surgical blood loss, cancer diagnostics, constipation, depression, insomnia, mastitis, OB diagnostics (for placental insufficiency), osteoporosis, placenta delivery, and wound healing/inflammation.

DETAILED DESCRIPTION

The present invention relates to compounds represented by the structural Formula (I):

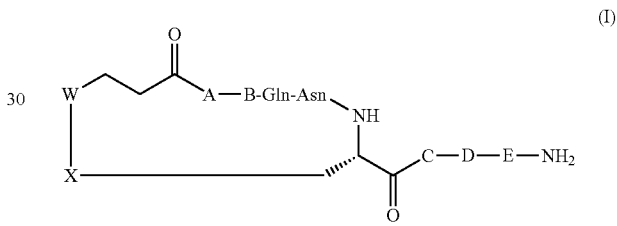

or pharmaceutically acceptable salts thereof,
wherein:
W and X are independently selected from $CH_2$ and S, but may not both be $CH_2$;
A is an amino acid selected from: alanine substituted on the side chain with a 5- or 6-membered heteroaromatic ring; Tyrosine; and Phenylalanine substituted on the phenyl ring, for example at the 4-position of the phenyl ring, with halogen, $C_{1-4}$ alkoxy, $C_{1-4}$ alkylhydroxy, $C_{1-4}$ alkyl or amino;
B is an amino acid selected from: isoleucine; and glycine substituted on the α-carbon with $C_{4-6}$ cycloalkyl;
C is an amino acid selected from: proline, wherein proline is optionally substituted, for example at the 4-position, on the side chain with hydroxyl, $C_{1-4}$ alkoxy, halogen or azide; and proline wherein the proline side chain is optionally interrupted by a heteroatom and which optionally interrupted side chain is optionally substituted with $C_{1-4}$ alkyl;
D is an amino acid selected from: leucine; homoleucine; isoleucine; and glycine substituted on the α-carbon with $C_{4-6}$ cycloalkyl; and
E is an amino acid selected from: glycine and azaglycine,
with the proviso that if C is 4-hydroxyproline, then A must be either phenylalanine substituted on the phenyl ring with halogen, or $C_{1-4}$ alkylhydroxy, and if C is 4-hydroxyproline and A is phenylalanine substituted on the phenyl ring with halogen, then either B or D must be glycine substituted on the α-carbon with $C_{4-6}$ cycloalkyl, or D must be isoleucine,
with the further proviso that if A is phenylalanine substituted on the phenyl ring with $C_{1-4}$ alkyl or halogen, then C must be proline or proline substituted on the side chain with halogen, with the further proviso that if A is phenylalanine substituted on the phenyl ring with halogen, then either B or D must be glycine substituted on the α-carbon with $C_{4-6}$ cycloalkyl, or D must be isoleucine.

Provided herein are further compounds represented by Formula I above wherein A is 4-halophenylalanine, for example, Cpa (4-chlorophenylalanine); 4-bromophenylalanine, or wherein A is alanine substituted on the side chain with a 5- or 6-membered heteroaromatic ring, for example, Ala(2-Fur) (2-furylalanine), Ala(3-Fur) (3-furylalanine); 2-Thi (2-thienylalanine); 3-Thi (3-thienylalanine); 2- or 3-pyrrolylalanine; 2-, 3- or 4-pyridylalanine; 2-, 4- or 5-imidazolylalanine; 2-. 4- or 5-thiazolylalanine; 2- or 5-thiadiazolyl; 5-tetrazolyl; and the like. Also provided herein are further compounds represented by Formula I above wherein A is tyrosine, or wherein A is phenylalanine substituted at the 4-position of the phenyl ring with $C_{1-4}$ alkoxy groups or with an amino group, for example, Tyr(Me) (4-methoxyphenylalanine); 4-ethoxyphenylalanine; Aph (4-aminophenylalanine); 4-N,N-dimethylaminophenylalanine; and the like. Also provided herein are further compounds represented by Formula I above wherein A is phenylalanine substituted at the 4-position on the phenyl ring with $C_{1-4}$ alkylhydroxyl, $C_{1-4}$ alkyl or halo, for example, Phe(4-Et) (4-ethylphenylalanine); 4-methylphenylalanine; Phe(4-$CH_2OH$) (4-hydroxymethylphenylalanine); 4-hydroxyethylphenylalanine; Phe(Br) (4-bromophenylalanine); 4-chlorophenylalanine; 4-fluorophenylalanine; and the like.

Provided herein are further compounds represented by Formula I above wherein B is isoleucine, or is glycine substituted with $C_{4-6}$ cycloalkyl, such as Gly(cPe) (cyclopentylglycine), Gly(cBu) (cyclobutylglycine), cyclohexylglycine; and the like.

Provided herein are further compounds represented by Formula I above wherein C is proline, optionally substituted at the 4-position of the proline ring with hydroxy, $C_{1-4}$ alkoxy, halo, or azido groups, for example, Hyp (4-hydroxyproline); Hyp(Me) (4-methoxyproline); Pro(F) (4-fluoroproline); Pro($N_3$) (4-azidoproline), and the like. Also provided herein are further compounds represented by Formula I above wherein B is proline interrupted in the proline ring with a heteroatom, and optionally substituted on the proline ring with $C_{1-4}$ alkyl, for example, Thz (4-thiaproline) or Dmt (5,5-dimethylthiaproline), and the like.

Provided herein are further compounds represented by Formula I above wherein D is leucine, Hol (homoleucine), isoleucine, and glycine substituted with $C_{4-6}$ cycloalkyl, such as Gly(cPe) (cyclopentylglycine) Gly(cBu) (cyclobutylglycine), cyclohexylglycine; and the like.

Provided herein are further compounds represented by Formula I above wherein E is glycine or AzGly (azaglycine).

Also provided herein are compounds as described above by general structural Formula I, and specific structural variants thereof, for use as pharmaceuticals. Also provided herein are pharmaceutical compositions comprising a therapeutically effective amount of at least one compound as described above as an active ingredient, in association with at least one pharmaceutically acceptable adjuvant, diluent or carrier.

For the purposes of the present invention, the following terminology is used.

$C_{1-4}$ alkyl denotes a substituent having from one to four carbon atoms, including iso-, sec-, and tert-configurations, as the expression is not related to the binding site of the alkyl chain in question or the structural isomers thereof.

$C_{4-6}$ cycloalkyl denotes a carbocyclic ring system containing from four to six carbon atoms. The ring system may contain unsaturated bonds between carbon atoms, to include, for example, cyclohexenyl, cyclopentenyl, cyclohexadienyl and the like.

A five-membered heteroaromatic ring system is a monocyclic aromatic ring system having five ring atoms, wherein 1, 2, 3 or 4 ring atoms are independently selected from N, O and S. Such ring systems can be, for example, thienyl, furyl, imidazolyl, pyrrolyl, pyrazolyl, thiazolyl, thiadiazolyl, tetrazolyl, and the like.

A six-membered heteroaromatic ring system is a monocyclic aromatic ring system having six ring atoms, wherein 1, 2, 3 or 4 ring atoms are independently selected from N, O and S. Such ring systems can be, for example, pyridyl, pyrazinyl, pyrimidinyl, pyridazinyl, and the like.

Substituent moieties may be, for example, halogen (fluorine, chlorine, bromine) atoms, and alkyl, cycloalkyl, hydroxy (—OH), alkoxy (—O-alkyl), alkylthio (—S-alkyl), alkylhydroxy (-alkyl-OH), azide ($N_3$), amino (—$NR_1R_2$, wherein $R_1$ and $R_2$ can be independently hydrogen or $C_{1-4}$ alkyl) or 5- or 6-membered heteroaromatic groups.

Examples of pharmaceutically acceptable salts comprise acid addition salts, e.g. a salt formed by reaction with hydrohalogen acids such as hydrochloric acid and mineral acids, such as sulphuric acid, phosphoric acid and nitric acid, as well as aliphatic, alicyclic, aromatic or heterocyclic sulphonic or carboxylic acids such as formic acid, acetic acid, propionic acid, succinic acid, glycolic acid, lactic acid, malic acid, tartaric acid, citric acid, benzoic acid, ascorbic acid, maleic acid, hydroxymaleic acid, pyruvic acid, p-hydroxybenzoic acid, embonic acid, methanesulphonic acid, ethanesulphonic acid, hydroxyethanesulphonic acid, halobenzenesulphonic acid, trifluoroacetic acid, trifluoromethanesulphonic acid, toluenesulphonic acid and naphthalenesulphonic acid.

In particular, the description relates to, but is not limited to, particular illustrative compounds, such as those disclosed below.

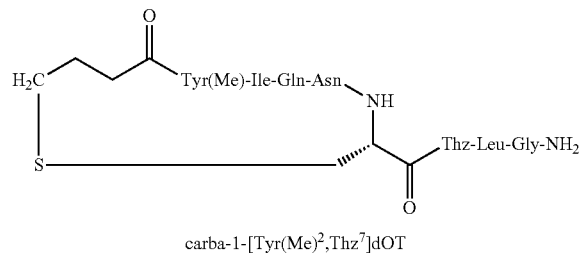

carba-1-[Tyr(Me)$^2$,Thz$^7$]dOT

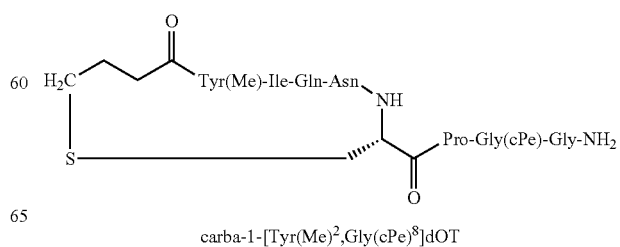

carba-1-[Tyr(Me)$^2$,Gly(cPe)$^8$]dOT

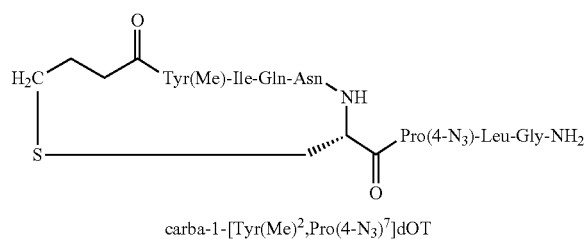
carba-1-[Tyr(Me)², Pro(4-N₃)⁷]dOT
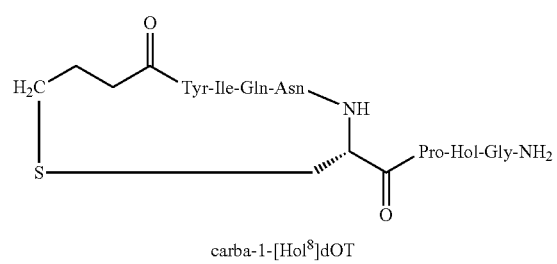
carba-1-[Hol⁸]dOT
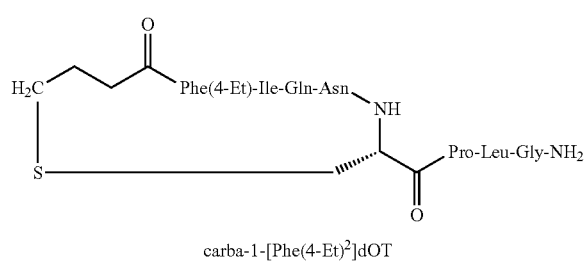
carba-1-[Phe(4-Et)²]dOT
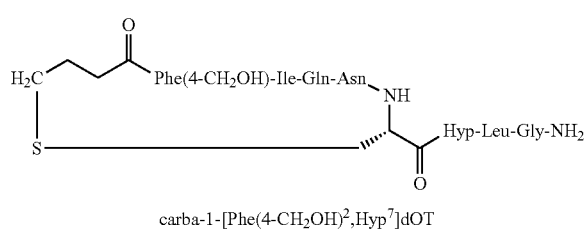
carba-1-[Phe(4-CH₂OH)², Hyp⁷]dOT
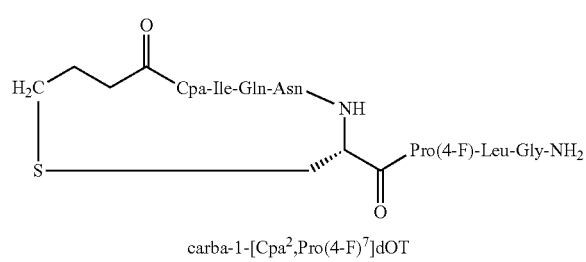
carba-1-[Cpa², Pro(4-F)⁷]dOT
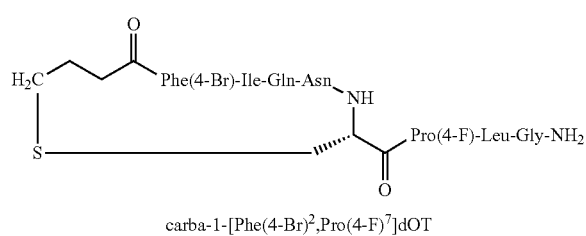
carba-1-[Phe(4-Br)², Pro(4-F)⁷]dOT
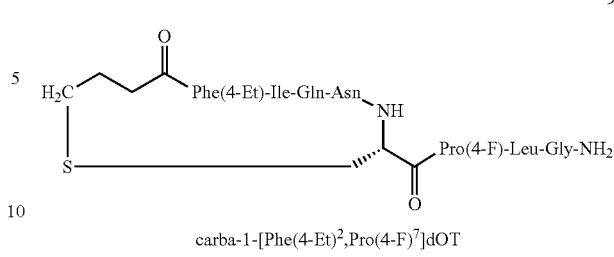
carba-1-[Phe(4-Et)², Pro(4-F)⁷]dOT
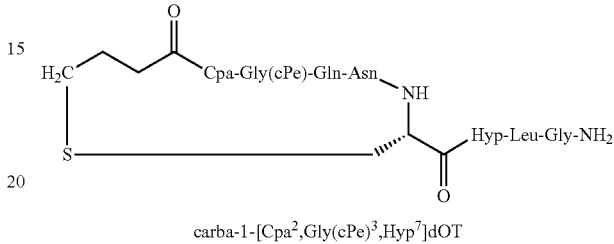
carba-1-[Cpa², Gly(cPe)³, Hyp⁷]dOT
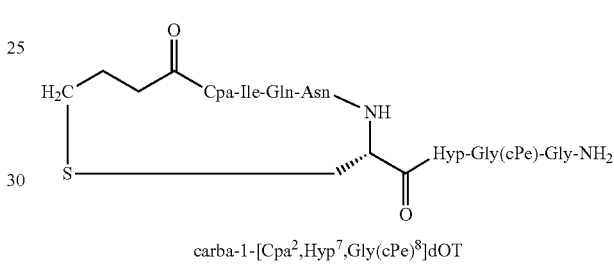
carba-1-[Cpa², Hyp⁷, Gly(cPe)⁸]dOT
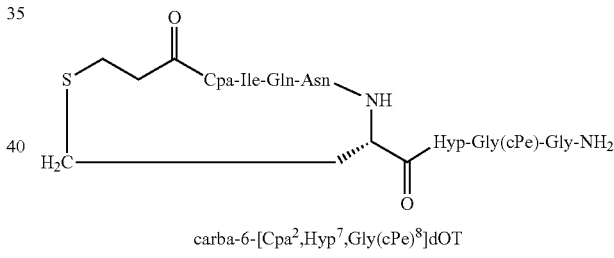
carba-6-[Cpa², Hyp⁷, Gly(cPe)⁸]dOT
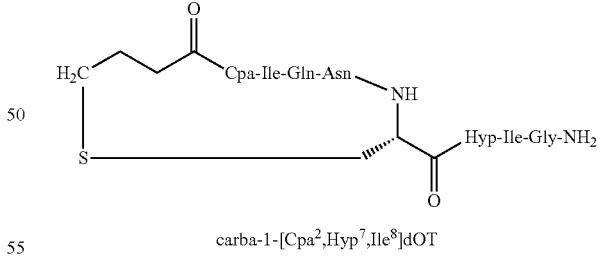
carba-1-[Cpa², Hyp⁷, Ile⁸]dOT
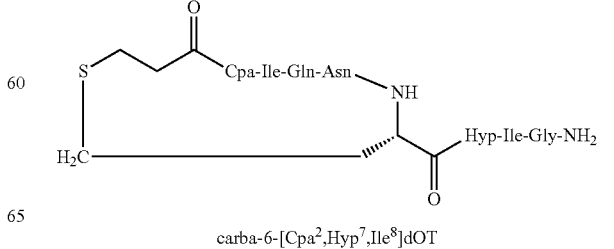
carba-6-[Cpa², Hyp⁷, Ile⁸]dOT

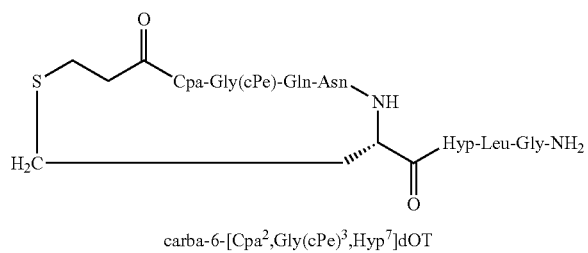

carba-6-[Cpa², Gly(cPe)³, Hyp⁷]dOT

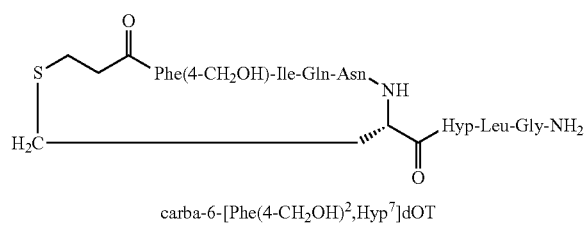

carba-6-[Phe(4-CH₂OH)², Hyp⁷]dOT

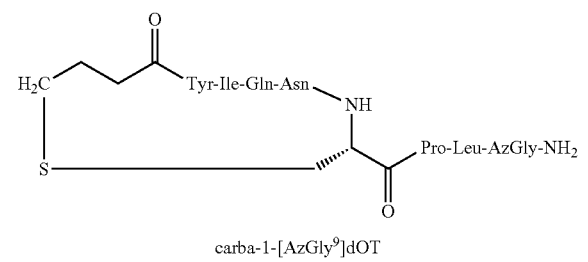

carba-1-[AzGly⁹]dOT

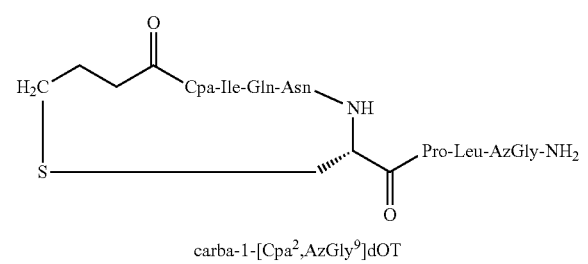

carba-1-[Cpa², AzGly⁹]dOT

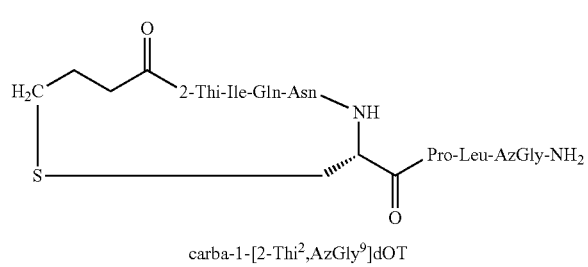

carba-1-[2-Thi², AzGly⁹]dOT

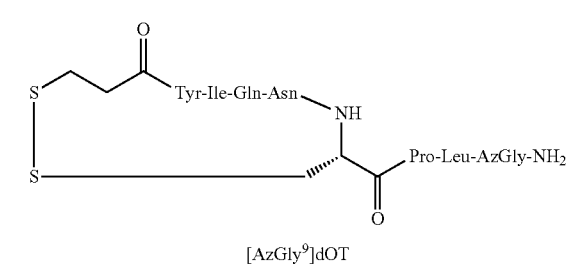

[AzGly⁹]dOT

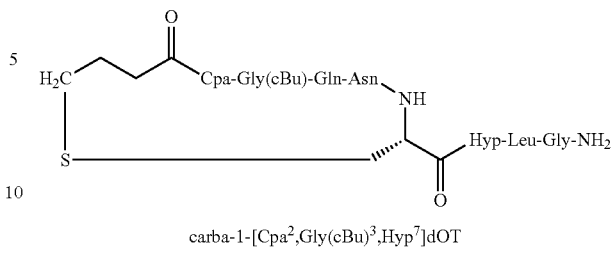

carba-1-[Cpa², Gly(cBu)³, Hyp⁷]dOT

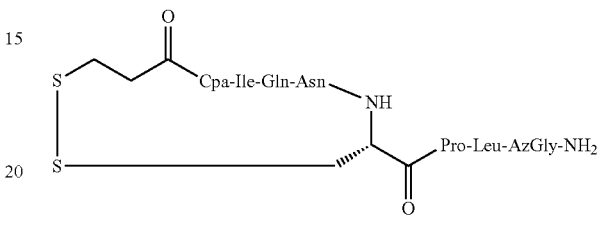

[Cpa², AzGly⁹]dOT

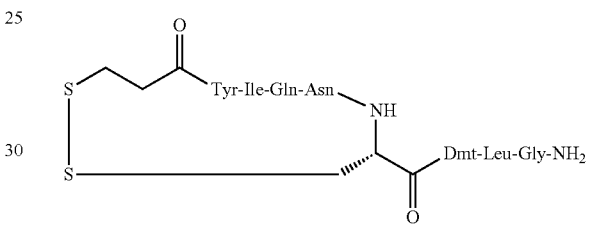

[Dmt⁷]dOT

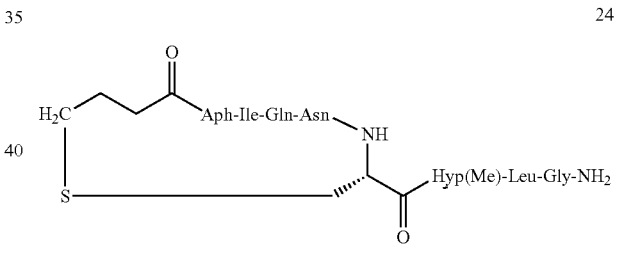

carba-1-[Aph², Hyp(Me)⁷]dOT or pharmaceutically acceptable salts thereof.

Furthermore the present invention relates to a compound as set forth above for the use as a pharmaceutical.

Accordingly, the present invention also relates to a pharmaceutical composition comprising a compound as set forth above as active ingredient in association with a pharmaceutically acceptable adjuvant, diluent or carrier.

The pharmaceutical composition may be adapted for oral, intravenous, intramuscular, topical, intraperitoneal, nasal, buccal, intraocular, intra-aural, sublingual or subcutaneous administration or for administration via the respiratory tract e.g. in the form of an aerosol or an air-suspended fine powder. The composition may thus for instance be in the form of tablets, capsules, powders, microparticles, granules, syrups, suspensions, solutions, transdermal patches or suppositories.

It should be noted that the composition according to the present invention may optionally include two or more of the above outlined compounds.

The present pharmaceutical composition may optionally comprise e.g. at least one further additive selected from a disintegrating agent, binder, lubricant, flavouring agent, preservative, colourant and any mixture thereof. Examples of such and other additives are found in 'Handbook of Pharmaceutical Excipients'; Ed. A.H. Kibbe, 3$^{rd}$ Ed., American Pharmaceutical Association, USA and Pharmaceutical Press UK, 2000.

The present pharmaceutical composition may be adapted for subcutaneous, intravenous or intramuscular administration, for example. It may comprise a sterile aqueous preparation of the compounds of the invention preferably isotonic with the blood of the recipient. This aqueous preparation may be formulated according to known methods using suitable dispersing or wetting agents and suspending agents. The intravenous formulation DURATOCIN® (carbetocin) is exemplary of a suitable pharmaceutical formulation applicable also for the inventive compounds disclosed herein. Water, Ringer's solution, and isotonic sodium chloride solution are exemplary acceptable diluents. The preparation may also include excipients such as sodium phosphate, citric acid, sodium chloride, glycerine, sorbitol solution, methylparaben, propylparaben and chlorobutanol.

In addition, the present invention relates to use of a compound as outlined above for, or for the manufacture of a medicament for, treatment of one or more medical conditions such as abdominal pain, irritable bowel syndrome (IBS), autism, erectile dysfunction, female sexual dysfunction, labor induction and maintenance, lactation induction and maintenance, postpartum hemorrhage, Post Traumatic Stress Disorder (PTSD), pain, anxiety, surgical blood loss, cancer diagnostics, constipation, depression, insomnia, mastitis, OB diagnostics (for placental insufficiency), osteoporosis, placenta delivery, and wound healing/inflammation. Herein, the term anxiety includes anxiety disorder. Anxiety disorder includes the sub indications generalized anxiety disorder, panic disorder, agoraphobia, phobias, social anxiety disorder, obsessive-compulsive disorder, post-traumatic stress disorder, and separation anxiety.

In another embodiment the invention relates to a method for treatment of abdominal pain, irritable bowel syndrome (IBS), autism, erectile dysfunction, female sexual dysfunction, labor induction and maintenance, lactation induction and maintenance, postpartum hemorrhage, Post Traumatic Stress Disorder (PTSD), pain, anxiety, surgical blood loss, cancer diagnostics, constipation, depression, insomnia, mastitis, OB diagnostics (for placental insufficiency), osteoporosis, placenta delivery, and wound healing/inflammation.

The typical dosage of the compounds according to the present invention varies within a wide range and will depend on various factors such as the individual needs of each patient and the route of administration. A physician of ordinary skill in the art will be able to optimise the dosage to the situation at hand.

For example, if the composition of the invention is for post partum hemorrhage (for example, for intravenous or intramuscular administration), a typical dose may be in the range of 0.5 to 200 µg/kg body weight. The skilled person or physician may consider relevant variations to this dosage range and practical implementations to accommodate the situation at hand.

In a further example, the composition of the invention may be administered as an intranasal dosage form, for example, for the treatment of Irritable Bowel Syndrome, lactation promotion and maintenance or sexual dysfunction. In this example it may be administered in divided dosages, for example, into 1, 2 or 3 sub-doses (e.g., puffs), for example, delivered to one or both nostrils. An example dosage for administration by an intranasal route may be 0.05-15.0 µg/kg body weight.

In a further example, the composition of the invention may be for subcutaneous (sc), intranasal, or buccal administration, for example to treat anxiety disorder or depression. An example dosage for subcutaneous (sc), or buccal administration is 0.5-1000 µg/kg body weight. The dosage may be, for example, for administration as many times a day as needed, for example, once or twice a day.

The abbreviations used are:
AcOH acetic acid
Boc tert-butoxycarbonyl
Bua butyric acid
$CH_3CN$ Acetonitrile
DCC N,N'-dicyclohexylcarbodiimide
DCM dichloromethane
DIC N,N'-diisopropylcarbodiimide
DIPEA N,N-diisopropylethylamine
DMF N,N-dimethylformamide
Fmoc 9-fluorenylmethoxycarbonyl
h hour(s)
HBTU  O-(benzotriazol-1-yl)-N,N,N',N'-tetramethyluronium hexafluorophosphate
HOBt 1-hydroxybenzotriazole
HPLC high performance liquid chromatography
MeOH Methanol
NMM 4-methylmorpholine
PyBOP benzotriazol-1-yloxy trispyrrolidinephosphonium hexafluorophosphate
tBu tert-butyl
tBuOH tert-butylalcohol
TFA trifluoroacetic acid
TIS triisopropylsilane
Trt trityl [triphenylmethyl, $(C_6H_5)_3C—$]

Unless otherwise specified L-amino acids were used and conventional amino acid terminology is adhered to.

Experimental (Synthesis)

Amino acid derivatives and resins were purchased from commercial providers (Bachem, BioQuadrant, ChemImpex, Novabiochem, Peptides International, RSP Amino Acids and Synthetech). Fmoc-Cys(t-butoxycarbonylpropyl)-OH and Fmoc-Hcy(t-butoxycarbonylethyl)-OH were synthesised according to literature [Prochazka et al., Collect. Czech. Chem. Commun., 57, (1992), 1335 and Wisniewski et al. in WO 03/072597]. Other chemicals and solvents were provided from Sigma-Aldrich, Fluka and Acros Organics.

The compounds herein were synthesised by standard methods in solid phase peptide chemistry utilising Fmoc methodology. All coupling of Fmoc-protected amino acids were mediated with DIC/HOBt/DMF. Removal of the Fmoc group was performed with 20% piperidine in DMF.

Unless otherwise provided, all reactions were performed at room temperature. In addition to the references cited supra, the following standard reference literature provides further guidance on general experimental set up, as well as on the availability of required starting material and reagents:

Kates and Albericio, Eds., "Solid Phase Synthesis: A Practical Guide," Marcel Dekker, New York, Basel, 2000;
Stewart and Young, "Solid Phase Synthesis," Pierce Chemical Company, 1984;
Bisello, et al., J. Biol. Chem., (1998), 273, 22498-22505; and Merrifield, J. Am. Chem. Soc. (1963), 85, 2149-2154.

Purity of the synthesised peptide may be determined by analytical reverse phase HPLC. Structural integrity of the peptides may be confirmed using amino acid analysis and electrospray mass spectrometry.

All amino acid couplings followed Fmoc methodology unless otherwise specified.

The amino acid derivative introduced in the 6 position was one of: Fmoc-Cys(Trt)-OH; Fmoc-Hcy(t-butoxycarbonylethyl)-OH or Fmoc-Cys(t-butoxycarbonylpropyl)-OH. Peptide analogues where position 6 was Fmoc-Cys(Trt)-OH required coupling of Mpa(Trt)-OH to the N-terminus of the resin-bound octapeptide residue.

The peptides synthesised using a Rink amide resin support were cleaved from the resin, together with any acid labile protecting groups such as Boc, trityl and t-butyl, with TFA/TIS/$H_2O$ 95/2.5/2.5 (v/v/v) solution. Said peptides were cyclised after cleavage of the peptide from the resin.

Cyclisation of the linear nonapeptide through disulfide (ring) formation was achieved by oxidation of linear peptides dissolved in 10% TFA (aq) with iodine. Cyclisation of the linear nonapeptide through amide bond formation was achieved by mediation with HBTU/DIPEA/DMF or PyBOP/DIPEA/DMF at a high dilution.

Peptides were purified by preparative HPLC in triethylammonium phosphate buffers (aq) and desalted with acetic acid (aq)/acetonitrile buffer system. The fractions with a purity exceeding 97% were pooled and lyophilised.

In all syntheses analytical HPLC was performed on a waters 600 Liquid Chromatograph using a Vydac C18, 5 μm, 4.6×250 mm column at a flow rate of 2 ml/min. Preparative HPLC was performed on a Waters 2000 Liquid Chromatograph using a PrePak 47×300 mm cartridge at a flow rate of 100 ml/min. Final compound analysis was performed on a 1100 Agilent Liquid Chromatograph using a Vydac C18, 5 μm, 2.1×250 mm column at a flow rate of 0.3 ml/min. Mass spectra were recorded on a Finnigan MAT spectrometer.

The following detailed examples are provided to further illustrate the synthesis:

Preparation of Compound 7; carba-1-[$Cpa^2$,Pro(4-F)$^7$]dOT

The amino acid derivatives used were Fmoc-Gly-OH, Fmoc-Leu-OH, Fmoc-Pro(4-F)—OH (BioQuadrant), Fmoc-Cys(t-butoxycarbonylpropyl)-OH, Fmoc-Asn(Trt)-OH, Fmoc-Gln(Trt)-OH, Fmoc-Ile-OH and Boc-Cpa-OH (Synthetech). Derivatives with no manufacturer specified were obtained from Peptide International. Fmoc-Cys(t-butoxycarbonyl propyl)-OH was synthesized as above.

The fully protected peptide resin was manually synthesised, starting from 0.5 g (0.125 mmol) of Tentagel Rink Amide resin (Peptide International). DIC/HOBt/DMF mediated single couplings with a 3-fold excess of amino acid derivatives were performed. The Fmoc groups were removed with 20% piperidine in DMF. Upon completion of the solid phase synthesis, the resin was treated with a TFA/TIS/$H_2O$ 96/2.5/1.5 (v/v/v) solution (30 ml) for 1.5 h and filtered off. The filtrate was concentrated in vacuo and the crude linear peptide was precipitated with diethyl ether. The precipitate was dissolved in DMF (150 ml) and DIPEA (0.174 ml) and HBTU (50 mg) were added to the vigorously stirred solution. The reaction was monitored by analytical HPLC. The reaction solution was concentrated in vacuo and the residue was dissolved in AcOH/$CH_3CN$/$H_2O$. The mixture was loaded onto an HPLC column and purified using a triethylammonium phosphate buffer with pH 5.2. The compound was eluted with a gradient of acetonitrile. The fractions with a purity exceeding 97% were pooled, diluted with water (2 volumes), and loaded onto a column pre-equilibrated with 2% AcOH (aq). The desired compound was eluted with a fast (3%/min) gradient of $CH_3CN$. The fractions containing the desired product were pooled and lyophilised. 57.9 mg (~40% yield, based on the loading of the starting resin and assuming 85% peptide content) of white amorphous powder was obtained. HPLC: Rt=12.4 min, gradient: 5% B for 0.5 min., 5→40% B in 0.5 min, 40→60% B over 20 min and 100% B for 5 min., t=40° C., solvent A 0.01% TFA (aq), solvent B 70% $CH_3CN$, 0.01% TFA (aq); Purity: 99.6%; MS (M+H$^+$): expected 1010.4, observed 1010.5.

Preparation of Compound 12; carba-6-[$Cpa^2$,$Hyp^7$, Gly(cPe)]dOT

The amino acid derivatives used were Fmoc-Gly-OH, Fmoc-Gly(cPe)-OH, Fmoc-Hyp(tBu)-OH (Novabiochem), Fmoc-Hcy(t-butoxycarbonylethyl)-OH, Fmoc-Asn(Trt)-OH, Fmoc-Gln(Trt)-OH, Fmoc-Ile-OH and Boc-Cpa-OH (Synthetech). Derivatives with no manufacturer specified were obtained from Peptide International. Fmoc-Hcy(t-butoxycarbonyl ethyl)-OH was synthesized as above.

The fully protected peptide resin was manually synthesized starting from 0.2 g of Tentagel Rink resin (0.05 mmol, Peptide International). DIC/HOBt/DMF mediated single couplings with a 3-fold excess of amino acid derivatives were performed. The Fmoc groups were removed with 20% piperidine in DMF. Upon completion of the solid phase synthesis, the resin was treated with a TFA/TIS/$H_2O$ 96/2.5/1.5 (v/v/v) solution (20 ml) for 1.5 h and filtered off. The filtrate was concentrated in vacuo and the crude linear peptide was precipitated with diethyl ether. The precipitate was dissolved in DMF (100 ml) and DIPEA (0.07 ml) and HBTU (20 mg) were added to the vigorously stirred solution. The reaction was monitored by analytical HPLC. The reaction solution was concentrated in vacuo and the residue was dissolved in AcOH/$CH_3CN$/$H_2O$. The mixture was loaded onto an HPLC column and purified using a triethylammonium phosphate buffer with pH 5.2. The compound was eluted with a gradient of acetonitrile. The fractions with a purity exceeding 97% were pooled, diluted with water (2 volumes), and loaded onto a column pre-equilibrated with 2% AcOH (aq). The desired compound was eluted with a fast (3%/min) gradient. The fractions containing the desired product were pooled and lyophilised.

40.0 mg (~66% yield, based on the loading of the starting resin and assuming 85% peptide content) of white amorphous powder was obtained. HPLC: Rt=10.8 min, gradient: 5% B for 0.5 min., 5→0.40% B in 0.5 min, 40→0.60% B over 20 min and 100% B for 5 min., t=40° C., solvent A 0.01% TFA (aq), solvent B 70% $CH_3CN$, 0.01% TFA (aq); Purity: 100.0%; MS (M+H$^+$): expected 1020.5, observed 1020.1.

Preparation of Compound 20; [AzGly$^9$]dOT

The compound was obtained by fragment condensation of the fully protected N-terminal heptapeptide carboxylic acid and the C-terminal dipeptide H-Leu-AzGly-$NH_2$. The amino acid derivatives used were Fmoc-Cys(Trt)-OH, Fmoc-Asn(Trt)-OH, Fmoc-Gln(Trt)-OH, Fmoc-Ile-OH, Fmoc-Tyr(tBu)-OH and Mpa(Trt)-OH (Peptides International) for the heptapeptide and Boc-Leu-OH (Bachem) for the C-terminal dipeptide. Derivatives with no manufacturer specified were obtained from Peptide International.

The fully protected heptapeptide resin was manually synthesized, starting from 1.5 g (0.9 mmol) of H-Pro-2-ClTrt resin (Novabiochem). DIC/HOBt/DMF mediated single couplings with a 3-fold excess of amino acid derivatives were performed. The Fmoc groups were removed with 20% piperidine in DMF. The protected (1-7) peptide was cleaved from the resin with 30% HFIP/DCM (60 ml) for 1.5 h. The solvents were evaporated and the product was precipitated with diethyl ether and used in the subsequent fragment condensation without further purification. The C-terminal dipeptide was synthesized as Boc-Leu-AzGly-NH$_2$ by coupling Boc-Leu-OH with semicarbazide (H$_2$N—NH—CO—NH$_2$—HCl, Aldrich) mediated by DCC/DCM/DIPEA. The dipeptide (0.46 g) was treated with TFA/DCM (40 ml) for 1 h. The solvents were evaporated and the residue was dissolved in DMF (5 ml). A solution of heptapeptide (1.67 g) in DMF (10 ml) was then added followed by DIPEA (3 ml) and PyBOP (0.546 g). After 1 h the solvent was evaporated and the residue was treated with TIS/TFA 98/2 (v/v) cocktail (50 ml) for 1 h. The reaction mixture was concentrated in vacuo and the crude linear peptide was precipitated with diethyl ether. The precipitate was dissolved in neat TFA (50 ml), poured onto a magnetically stirred 5% aqueous acetonitrile (500 ml) solution and the peptide was oxidised by adding 0.1 M I$_2$ in methanol until yellow colour persisted. Excess of iodine was reduced with solid ascorbic acid (Sigma-Aldrich) and the pH of the solution was adjusted to about 4 by adding concentrated ammonia (aq). The mixture was loaded onto an HPLC column and purified using a triethylammonium phosphate buffer with pH 5.2. The compound was eluted with a gradient of acetonitrile. The fractions with a purity exceeding 97% were pooled, diluted with water (2 volumes), and loaded onto a column pre-equilibrated with 2% AcOH (aq). The desired compound was eluted with a fast (3%/min) gradient of acetonitrile. The fractions containing the desired product were pooled and lyophilised. 411.9 mg (~39% yield, based on the amount of the N-terminal heptapeptide used and assuming 85% peptide content) of white amorphous powder was obtained. HPLC: Rt=17.3 min, gradient: 0→20% B in 1 min, 20→40% B over 20 min and 100% B for 5 min., t=40° C., solvent A 0.01% TFA (aq), solvent B 70% CH$_3$CN, 0.01% TFA (aq); Purity: 100.0%; MS (M+H$^+$): expected 993.4, observed 993.2.

The other compounds were prepared by analogous variation of these synthetic procedures.

TABLE 1

Compounds prepared with the Formula (I)

| SEQ ID No. | W | X | A | B | C | D | E |
|---|---|---|---|---|---|---|---|
| 1 | CH$_2$ | S | Tyr (Me) | Ile | Thz | Leu | Gly |
| 2 | CH$_2$ | S | Tyr (Me) | Ile | Pro | Gly (cPe) | Gly |
| 3 | CH$_2$ | S | Tyr (Me) | Ile | Pro (4-N$_3$) | Leu | Gly |
| 4 | CH$_2$ | S | Tyr | Ile | Pro | Hol | Gly |
| 5 | CH$_2$ | S | Phe (4-Et) | Ile | Pro | Leu | Gly |
| 6 | CH$_2$ | S | Phe (4-CH$_2$OH) | Ile | Hyp | Leu | Gly |
| 7 | CH$_2$ | S | Cpa | Ile | Pro (4-F) | Leu | Gly |
| 8 | CH$_2$ | S | Phe (4-Br) | Ile | Pro (4-F) | Leu | Gly |
| 9 | CH$_2$ | S | Phe (4-Et) | Ile | Pro (4-F) | Leu | Gly |
| 10 | CH$_2$ | S | Cpa | Gly (cPe) | Hyp | Leu | Gly |
| 11 | CH$_2$ | S | Cpa | Ile | Hyp | Gly (cPe) | Gly |
| 12 | S | CH$_2$ | Cpa | Ile | Hyp | Gly (cPe) | Gly |
| 13 | CH$_2$ | S | Cpa | Ile | Hyp | Ile | Gly |
| 14 | S | CH$_2$ | Cpa | Ile | Hyp | Ile | Gly |
| 15 | S | CH$_2$ | Cpa | Gly (cPe) | Hyp | Leu | Gly |
| 16 | S | CH$_2$ | Phe (4-CH$_2$OH) | Ile | Hyp | Leu | Gly |
| 16 | CH$_2$ | S | Tyr | Ile | Hyp | Leu | AzGly |
| 18 | CH$_2$ | S | Cpa | Ile | Pro | Leu | AzGly |
| 19 | CH$_2$ | S | 2-Thi | Ile | Pro | Leu | AzGly |
| 20 | S | S | Tyr | Ile | Pro | Leu | AzGly |
| 21 | CH$_2$ | S | Cpa | Gly (cBu) | Hyp | Leu | Gly |
| 22 | S | S | Cpa | Ile | Pro | Leu | AzGly |
| 23 | S | S | Tyr | Ile | Dmt | Leu | Gly |
| 24 | CH$_2$ | S | Aph | Ile | Hyp (Me) | Leu | Gly |

Experimental (Biological Testing)

In Vitro Receptor Assays:

Agonist activities of illustrative compounds on the hOT receptor were determined in a transcriptional reporter gene assay by either transiently transfecting a hOT receptor expression DNA into a Chinese Hamster Ovary (CHO) cell line in concert with a reporter DNA containing intracellular calcium responsive promoter elements regulating expression of firefly luciferase, or by transfecting the same reporter DNA construct into a CHO cell line stably expressing the hOT receptor. See for example Boss et al., *J. Biol. Chem.*, (1996), 271(18), 10429-10432 for further guidance on this assay. Cells were exposed to serial dilutions of compounds diluted 10-fold per dose for 5 hours, followed by lysis of cells, determination of luciferase activity, and determination of compound efficacies and EC$_{50}$ values through non-linear regression. Carbetocin was used as an internal control in each experiment. The data displayed normal variation in individual assays performed.

The in vitro assay results ($EC_{50}$ value for hOT potency as the geometric mean expressed in nanomol/l (nM)) for the compounds specifically described herein were in the range of from about 0.01 nM to about 3.90 nM, for example, from about 0.01 nM to about 0.75 nM, or for example from about 0.01 nM to about 0.50 nM, or from about 0.01 nM to about 0.25 nM, or from about 0.01 nM to about 0.10 nM. Each compound tested was more potent at hOT than carbetocin in these assays.

The foregoing results indicate that compounds disclosed herein are within the scope of the invention and may for instance be useful in the safe and efficacious treatment of human beings for conditions including abdominal pain, irritable bowel syndrome (IBS), autism, erectile dysfunction, female sexual dysfunction, labor induction and maintenance, lactation induction and maintenance, postpartum hemorrhage, Post Traumatic Stress Disorder (PTSD), pain, anxiety, surgical blood loss, cancer diagnostics, constipation, depression, insomnia, mastitis, OB diagnostics (for placental insufficiency), osteoporosis, placenta delivery, and wound healing/inflammation.

The scope of the present invention is further defined in the following claims.

What is claimed is:

1. A compound represented by structural Formula I:

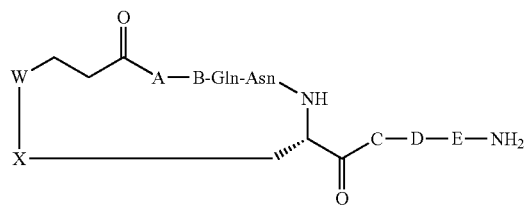

wherein

W and X are independently selected from $CH_2$ and S, but are not both $CH_2$;

A is an amino acid selected from: alanine substituted on the side chain with a 5- or 6-membered heteroaromatic ring; and phenylalanine substituted on the phenyl ring with halogen, $C_{3-4}$ alkoxy, $C_{1-4}$ alkylhydroxy, or $C_{3-4}$ alkyl;

B is an amino acid selected from: isoleucine; and glycine substituted on the α-carbon with $C_{4-6}$ cycloalkyl;

C is an amino acid selected from: proline, optionally substituted on the side chain with hydroxyl, $C_{1-4}$ alkoxy, halogen or azide, and proline having its side chain optionally interrupted by a heteroatom and which optionally interrupted side chain is optionally substituted with $C_{1-4}$ alkyl;

D is an amino acid selected from: leucine; homoleucine; isoleucine; and glycine substituted on the α-carbon with $C_{4-6}$ cycloalkyl; and E is an amino acid selected from: glycine and azaglycine, with the proviso that if C is 4-hydroxyproline, then A must be either phenylalanine substituted on the phenyl ring with halogen, or $C_{1-4}$ alkylhydroxy, and if C is 4-hydroxyproline and A is phenylalanine substituted on the phenyl ring with halogen, then either B or D must be glycine substituted on the α-carbon with $C_{4-6}$ cycloalkyl, or D must be isoleucine, with the further proviso that if A is phenylalanine substituted on the phenyl ring with $C_{1-4}$ alkyl or halogen, then C must be proline or proline substituted on the side chain with halogen, and with the further proviso that if A is phenylalanine substituted on the phenyl ring with halogen, then either B or D must be glycine substituted on the α-carbon with $C_{4-6}$ cycloalkyl, or D must be isoleucine.

2. The compound of claim 1, wherein A is 4-halophenylalanine.

3. The compound of claim 1, wherein A is alanine substituted on the side chain with a 5- or 6-membered heteroaromatic ring.

4. The compound of claim 1, wherein A is phenylalanine substituted with 4-hydroxymethyl.

5. The compound of claim 1, wherein B is isoleucine.

6. The compound of claim 1, wherein B is glycine substituted with cyclobutyl or cyclopentyl.

7. The compound of claim 1, wherein C is 4-hydroxyproline.

8. The compound of claim 1, wherein C is 4-fluoroproline.

9. The compound of claim 1, wherein C is proline.

10. The compound of claim 1, wherein D is leucine.

11. The compound of claim 1, wherein D is isoleucine.

12. The compound of claim 1, wherein D is glycine substituted with cyclobutyl or cyclopentyl.

13. The compound of claim 1, wherein E is glycine.

14. The compound of claim 1, wherein E is azaglycine.

15. A compound selected from the group consisting of:

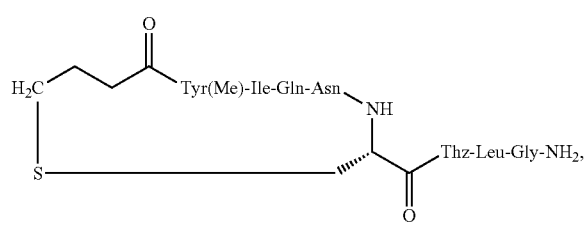

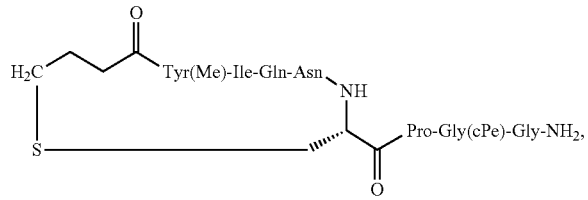

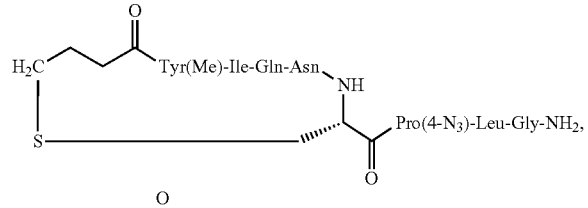

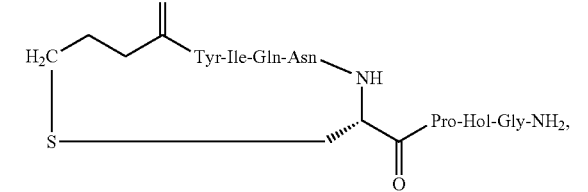

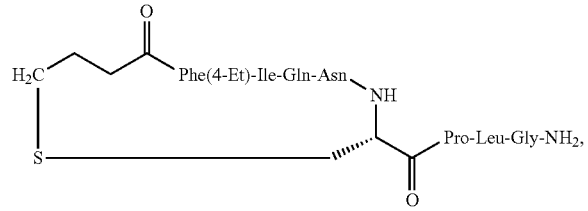

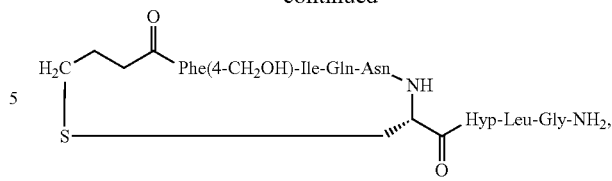

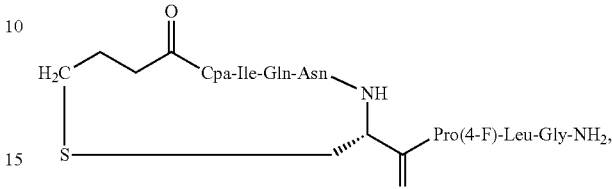

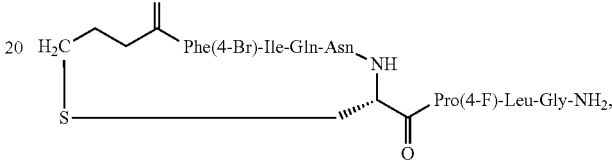

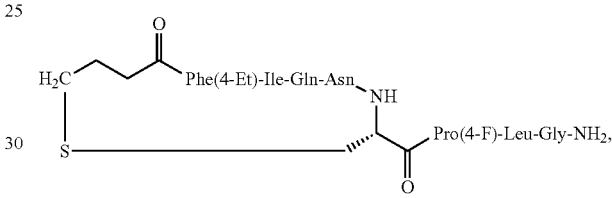

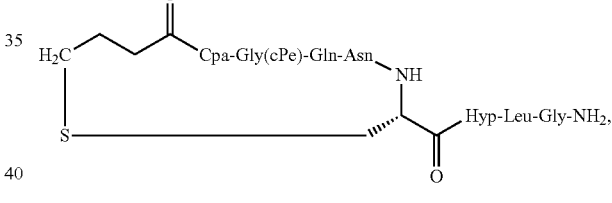

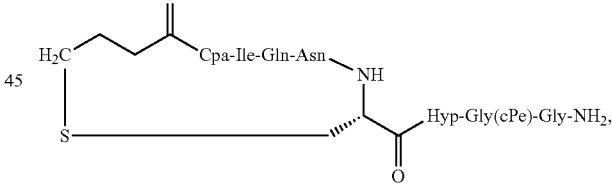

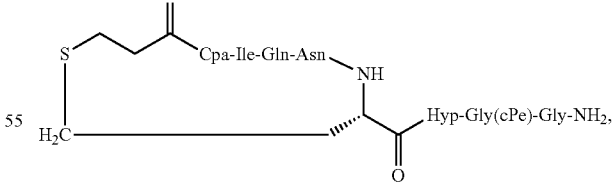

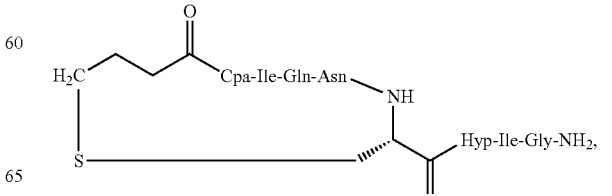

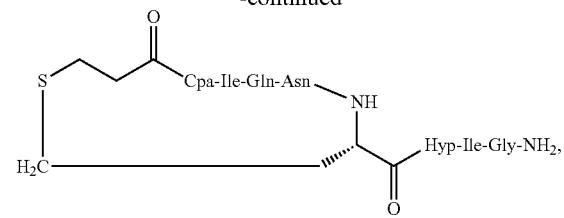

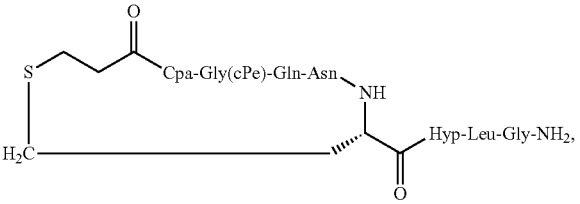

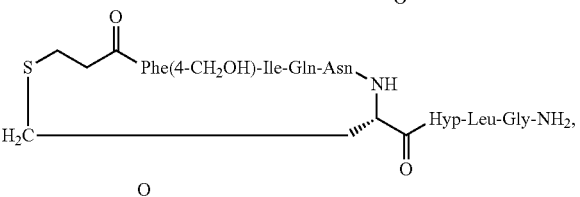

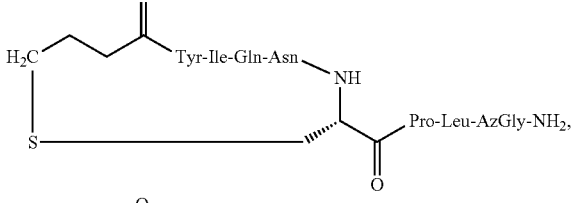

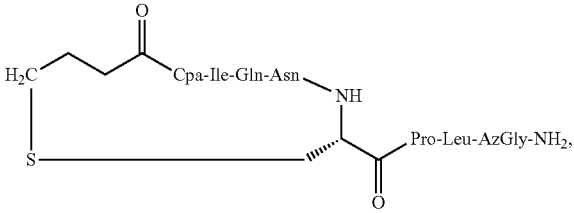

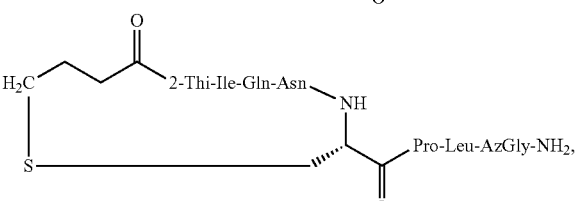

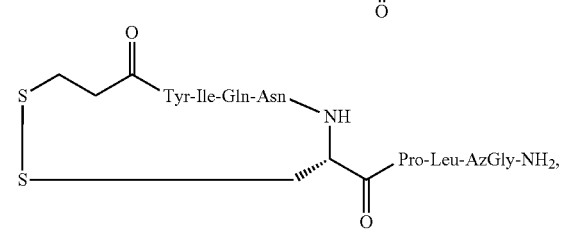

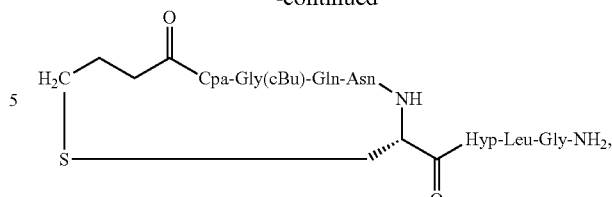

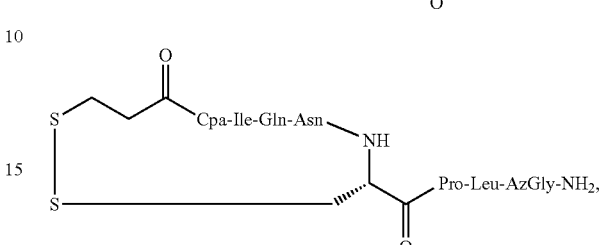

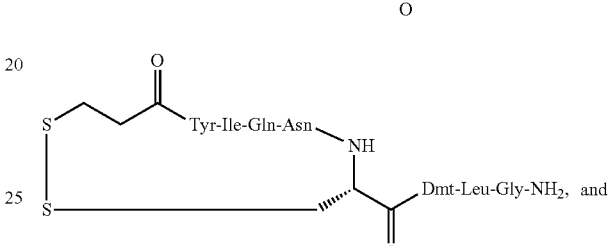

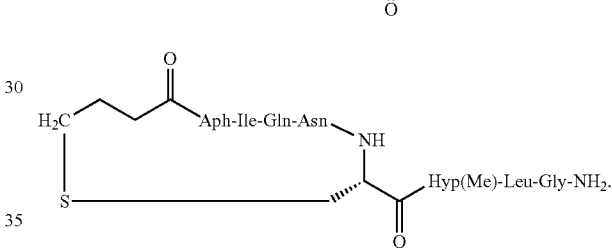

16. A pharmaceutical formulation comprising a therapeutically effective amount of a compound according to claim 1 as an active ingredient in association with a pharmaceutically acceptable adjuvant, diluent or carrier.

17. A method for treating a disorder in a patient, wherein the method comprises administering to a patient in need thereof, an effective amount of a compound according to claim 1, and wherein the disorder is a member selected from the group consisting of abdominal pain, irritable bowel syndrome, autism, erectile dysfunction, female sexual dysfunction, labor induction and maintenance, lactation induction and maintenance, postpartum hemorrhage, Post Traumatic Stress Disorder, pain, anxiety, surgical blood loss, cancer diagnostics, constipation, depression, insomnia, mastitis, osteoporosis, placenta delivery, and wound healing/inflammation.

* * * * *